(12) United States Patent  
Trabish

(10) Patent No.: US 12,171,522 B2  
(45) Date of Patent: Dec. 24, 2024

(54) MEDICAL DEVICES WITH PHOTODETECTORS AND RELATED SYSTEMS AND METHODS

(71) Applicant: Orthosensor Inc., Dania Beach, FL (US)

(72) Inventor: Masei Marty Trabish, Seoul (KR)

(73) Assignee: HOWMEDICA OSTEONICS CORP., Mahwah, NJ (US)

(*) Notice: Subject to any disclaimer, the term of this patent is extended or adjusted under 35 U.S.C. 154(b) by 197 days.

(21) Appl. No.: 17/894,547

(22) Filed: Aug. 24, 2022

(65) Prior Publication Data

US 2023/0066808 A1 Mar. 2, 2023

Related U.S. Application Data

(60) Provisional application No. 63/236,447, filed on Aug. 24, 2021.

(51) Int. Cl.
*A61B 5/00* (2006.01)
*H01L 31/0232* (2014.01)
*H01L 31/0384* (2006.01)
*B82Y 20/00* (2011.01)

(52) U.S. Cl.
CPC .......... *A61B 5/0059* (2013.01); *A61B 5/6801* (2013.01); *H01L 31/02322* (2013.01); *H01L 31/0384* (2013.01); *B82Y 20/00* (2013.01)

(58) Field of Classification Search
CPC ................ A61B 5/0059; A61B 5/6801; H01L 31/02322; H01L 31/0384
See application file for complete search history.

(56) References Cited

U.S. PATENT DOCUMENTS

| 2009/0054752 | A1 | 2/2009 | Jonnalagadda et al. |
| 2017/0316487 | A1* | 11/2017 | Mazed ............... G06Q 30/0241 |
| 2017/0354335 | A1 | 12/2017 | Bower et al. |

FOREIGN PATENT DOCUMENTS

| CN | 107209852 A | 9/2017 |
| TW | 202045091 A | 12/2020 |
| WO | 2019082120 A1 | 5/2019 |

OTHER PUBLICATIONS

Lee et al, "Toward all-day wearable health monitoring: An ultralow-power, reflective organic pulse oximetry sensing patch", Science Advances, Nov. 9, 2018. (9 pages).

* cited by examiner

*Primary Examiner* — Joel F Brutus
(74) *Attorney, Agent, or Firm* — Bookoff McAndrews, PLLC

(57) ABSTRACT

In one aspect, a medical device may be configured to couple to a body, the medical device comprising: a substrate configured to couple to a user's skin; a photodetector comprising an array of quantum dots, wherein the array of quantum dots includes a first quantum dot of a first size and a second quantum dot of a second size, wherein the first size is different from the second size; a first illuminator configured to emit light at a first range of wavelengths; and a second illuminator configured to emit light at a second range of wavelengths. The second range of wavelengths may be different from the first range of wavelengths.

20 Claims, 4 Drawing Sheets

MEDICAL DEVICES WITH PHOTODETECTORS AND RELATED SYSTEMS AND METHODS

CROSS-REFERENCE TO RELATED APPLICATIONS

This application claims the benefit of priority under 35 U.S.C. § 119 from U.S. Provisional Application No. 63/236,447, filed on Aug. 24, 2021, which is incorporated by reference herein in its entirety

TECHNICAL FIELD

Various aspects of the present disclosure relate generally to medical devices and related methods for detecting one or more physiological parameters from the surface of the skin, among other aspects. More specifically, at least certain embodiments of the present disclosure relate to systems, devices, and related methods for detecting physiological parameters using quantum dot photodiodes, among other aspects.

BACKGROUND

Photoplethysmography (PPG) is an optical technique used to detect volumetric changes in blood in peripheral circulation, among other physiological parameters. It is a low cost and non-invasive method that makes measurements at the surface of the skin. The technique provides valuable information used in clinical physiological measurement and monitoring. When light travels through biological tissues it is absorbed by bones, skin pigments, both venous and arterial blood, and other bodily tissue. Since light is more strongly absorbed by blood than the surrounding tissues, the changes in blood flow can be detected by PPG sensors as changes in the intensity of light. The voltage signal from PPG is proportional to the quantity of blood flowing through the blood vessels. Even small changes in blood volume can be detected using this method.

In PPG, a light source shines light into the human body and a sensor measures how the scattered light intensity changes with each pulse of blood flow. The scattered light intensity will change in time with respect to changes in blood flow or blood opacity associated with heart beats, breaths, blood oxygen level (SpO2), and the like. Such a sensing methodology may require the magnitude of light energy reaching the volume of flesh being interrogated to be steady and consistent so that small changes in the quantity of scattered photons can be attributed to varying blood flow.

A device such as a pulse oximeter provides for measuring enhanced optical pulsatile signals emitted by the changes in the volume of blood flowing through a user. The pulse oximeter typically has a pair of small light emitting diodes (LEDs) and a photodiode. The light from the LEDs passes through the tissue and is detected by the photodiode. One LED is red, with wavelength of approximately 660 nanometers (nm), and the other is infrared, with a wavelength of approximately 905, 910 or 940 nm. Absorption at these wavelengths differs significantly between hemoglobin and its deoxygenated form. Therefore, the ratio of oxyhemoglobin to deoxyhemoglobin can be calculated from the ratio of the absorption of the red and infrared light, i.e. the ratio of red light to infrared light absorption of pulsating components at the measuring site.

The basic form of PPG technology requires only a few optoelectronic components: a light source to illuminate the tissue (e.g. skin) and a photodetector to measure the small variations in light intensity associated with changes in perfusion in a catchment volume. The majority of PPG devices currently available rely on simple thresholding, or peak detection algorithms, to find principal peaks in a detected signal. However, these methods are typically unreliable when the detected signal is less than ideal. Particular problems may be encountered when the baseline of the AC signal component becomes noisy or complex, as can occur even with mild movement artifacts. A signal may be compromised by noise due to motion artifacts, especially artifacts caused by acceleration in the context of wearable PPG sensors.

Hence, there exists a need for an optical measurement device and a method for detecting a physiological parameter using an optical measurement device that seek to address at least one of the above problems or other problems in the art.

SUMMARY

Aspects of this disclosure relate to systems, devices, and methods for obtaining at least one physiological parameter measurement of a user. Each of the aspects disclosed herein may include one or more of the features described in connection with any of the other disclosed aspects.

According to one aspect, a medical device may be configured to couple to a body, and the medical device may comprise: a substrate configured to couple to a user's skin; a photodetector comprising an array of quantum dots, wherein the array of quantum dots includes a first quantum dot of a first size and a second quantum dot of a second size and the first size is different from the second size; a first illuminator configured to emit light at a first range of wavelengths; and a second illuminator configured to emit light at a second range of wavelengths. The second range of wavelengths is different from the first range of wavelengths.

In other aspects, the medical device may include one or more of the following features. At least one wire element may be positioned within the substrate, and the wire element may be electrically coupled to the photodetector, the first illuminator, and/or the second illuminator. A hydrogel layer may extend across the substrate, and the photodetector, the first illuminator, and the second illuminator may be positioned within the hydrogel layer. The medical device may further comprise a controller electronically coupled to the photodetector, the first illuminator, and the second illuminator. The first illuminator may be configured to emit green light; the second illuminator may be configured to emit red light; the first quantum dot may be configured to absorb only green light; and the second quantum dot may be configured to absorb only red light. The medical device may further comprise a third illuminator configured to emit infrared light; and a third quantum dot configured to absorb only infrared light. The first quantum dot may be a 5 nm diameter CdSe quantum dot; the second quantum dot may be a 7 nm diameter CdSe quantum dot; and the third quantum dot may be a 10 nm diameter PbS quantum dot. The array of quantum dots may be arranged in a single layer honeycomb structure in which each quantum dot of the array of quantum dots only boarders other quantum dots of a different size. The controller may be configured to measure a first physiological parameter when the first illuminator is activated and the second illuminator is deactivated, and the controller may be configured to use data from the photodetector to calculate the first physiological parameter, and the controller may be configured to measure a second physiological parameter when the second illuminator is activated and the first illuminator is deactivated, wherein the controller is configured to use data from the photodetector to calculate the second physiological parameter. The photodetector may include graphene and/or one or more titanium dioxide nanotube arrays. The medical device may further comprise a body coupled to the substrate, wherein the photodetector, the first illuminator, and the second illuminator are positioned within the body. The substrate may be a medical tape configured to couple to skin of a user. The photodetector may be positioned between the first illuminator and the second illuminator. The array of quantum dots may include at least 1000 quantum dots. The first quantum dot may comprise a plurality of first quantum dots arranged in a row, and wherein the second quantum dot may comprise a plurality of second quantum dots arranged in a row adjacent to the row of first quantum dots.

In other aspects, a medical device may be configured to couple to a body. The medical device may comprise a flexible substrate configured to couple to a user's skin; a photodetector comprising an array of quantum dots and one or more titanium dioxide nanotube arrays; a first illuminator configured to emit light at a first range of wavelengths; and a wire element positioned on the flexible substrate and configured to electrically couple the first illuminator to a controller.

In other aspects, the medical device may include one or more of the following features. The array of quantum dots may include a first quantum dot of a first size, a second quantum dot of a second size, and a third quantum dot of a third size; wherein the first size is larger than the second size and the second size is larger than the third size. The first quantum dot may be a 5 nm diameter CdSe quantum dot, the second quantum dot may be a 7 nm diameter CdSe quantum dot, and the third quantum dot may be a 10 nm PbS quantum dot. The medical device may be configured to measure at least one of: electrical activity of a user's heart, blood oxygen saturation, heart rate, respiration and/or cardiac output, blood pressure, and volumetric variations of blood circulation.

In other aspects, a method of measuring a physiological parameter using a medical device is disclosed. The medical device may comprise a flexible substrate configured to couple to a user's skin; a photodetector comprising an array of quantum dots; a first illuminator configured to emit light at a first range of wavelengths; and a second illuminator configured to emit light at a second range of wavelengths, wherein the second range of wavelengths is different from the first range of wavelengths. The method may comprise coupling the medical device to a body; activating a first quantum dot of the array of quantum dots; emitting light from the first illuminator towards the body; receiving reflected light at the first quantum dot; deactivating the first quantum dot; activating a second quantum dot of the array of quantum dots, wherein the second quantum dot is different from the first quantum dot and has a different size from the first quantum dot; emitting light from the second illuminator towards the body; and receiving reflected light at the second quantum dot.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Figure 1:
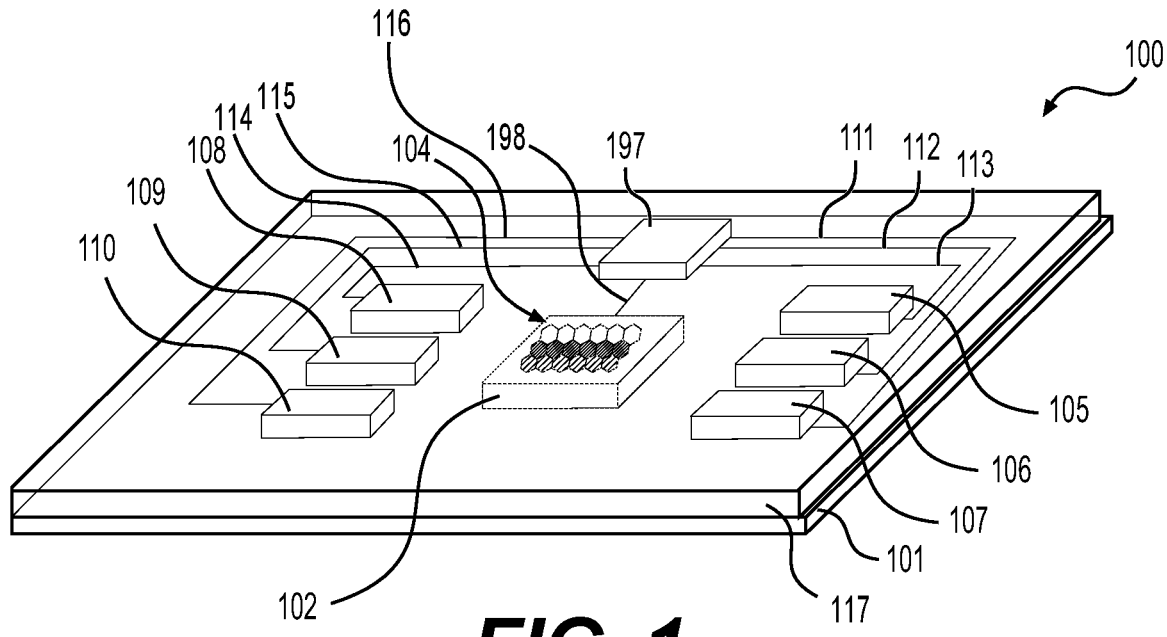
FIG. 1 is a perspective view of a wearable medical device, according to aspects of this disclosure.

The present disclosure is drawn to medical systems, devices, and methods for measuring one or more physiological parameters, among other aspects. Reference will now be made in detail to aspects of the present disclosure, examples of which are illustrated in the accompanying drawings. Wherever possible, the same or similar reference numbers will be used through the drawings to refer to the same or like parts. The term "coupled to tissue" may refer, for example, to adhering, fixing, attaching, clutching, or fastening, or otherwise secured to a user's body. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Photodetectors, also called photosensors or light sensors, are sensors of light or other electromagnetic radiation. A photo detector has a p-n junction that converts light photons into current. Photodiodes and photo transistors are a few examples of photo detectors.

Quantum dots are unique semiconductor nano-crystals that possess several useful properties such as photoluminescence (PL). Photoluminescence refers to absorption of light by a quantum dot at one wavelength and emission of light at a second wavelength. In some examples, quantum dots may be used in photodetectors for detecting light from light emitting diode (LED) light sources. Quantum dots are generally composed of two elements which have dramatically high quantum efficiencies when light is shined on them. For example, cadmium (Cd) and selenium (Se) may be combined to form clusters and create CdSe quantum dots. Lead (Pb) and sulfide (S) may be combined to form clusters and create PbS quantum dots. Zinc (Zn) and selenide (Se)

may be combined to form clusters and create ZnSe quantum dots. Also, many other elements known in the art may be used to form quantum dots, and this disclosure is not so limited to CdSe quantum dots, PbS quantum dots, and ZnSe quantum dots. As discussed below, photodetectors containing quantum dots may be designed to have high efficiency at detecting a particular wavelength range of light based on the size of the quantum dots used in the photodetector.

Since quantum dots may have a narrow absorption profile, or range of light wavelengths the quantum dot can detect, quantum dots may effectively filter out unwanted wavelengths of light without needing a separate light filter. A photodetector containing quantum dots without any filter may have increased sensitivity compared to a photodetector including a filter, since often a filter requires some loss of gain in the photodetector.

In the context of biosignals, the human body reduces the amount of green light that penetrates the skin from external light sources because of Melanin in the skin. Based on this, a green light source, applied to the human body, may be easier to detect than other light sources. A red light source may be used to measure heart rate, pulse oximetry, muscle oxygenation, blood flow, total hemoglobin, among other physiological parameters. An infrared light source may be used to measure skin layer thickness, bone thickness, and/or other physiological parameters. In some examples, an infrared light source may be used to calculate relative correction values for use in calibrating a sensor system, such as a system including a device with a photodetector and a light source. The use of quantum dots in photodetectors may help eliminate unwanted external white noise of light in wearable medical devices configured to measure one or more physiological parameters.

FIG. 1 shows a perspective view of an exemplary medical device 100. Medical device 100 may include a substrate 101 and a layer of material 117, such as hydrogel. Substrate 101 may be flexible and may be configured to adhere to a body of a user. Substrate 101 may be rectangular or any other suitable shape. In some examples, substrate 101 may be a non-woven medical tape, woven fabric medical tape, paper medical tape, zinc-oxide medical tape, silk surgical medical tape, plastic medical tape, or other adhesive fabric or material. A photodetector 102, illuminators 105-110, controller 197, and wire elements 112-116, 198 may be coupled to substrate 101, and layer of material 117 may cover and envelope all or a portion of: photodetector 102, illuminators 105-110, controller 197, and/or wire elements 112-116. In some examples, nets (not shown) may be coupled to substrate 101 and may be configured to electronically connect components of medical device 100 to controller 197. For example, a die (chip) of light emitting diodes (LEDs) may be used for one or more illuminators 105-110, the die may be several micrometers in length, and may include bonded cathodes and anodes to nets. In some examples, layer of material 117 may cover a portion of substrate 101. Wire element 198 may electronically couple photodetector 102 to controller 197, and each of wire elements 111-116 may electronically couple each of illuminators 105-110 to controller 197.

Illuminators 105-110 may be positioned adjacent to photodetector 102 and may be electronically connected to each other, controller 197, and/or photodetector 102 via wire elements 112-114, 198. Illuminators 105-110 may be light emitting diodes (LEDs) and/or may be other illuminators known in the art. In some examples, one or more of illuminators 105-110 may include quantum dots. One or more of illuminators 105-110 may emit infrared (IR) light which may have wavelengths $\lambda$ between 780 nm and 1 mm, green light which may have wavelengths $\lambda$ between 495 nm and 570 nm, and/or red light which may have wavelengths $\lambda$ between 620 nm and 750 nm. In some examples, illuminators 105, 108 may emit IR light, illuminators 106, 109 may emit green light, and illuminators 107, 110 may emit red light. Although medical device 100 is shown with six illuminators 105-110, in other examples medical device 100 may include 1, 2, 3, 4, 5, 7, 8, 9, or any other suitable amount of illuminators.

Wire elements 112-116, 198 may be nano-silver wires and may be printed onto substrate 101. In some examples, wire elements 112-116, 198 may have a diameter between approximately 5 nm and 100 nm. In some examples, wire elements 112-116, 198 may electrically couple photodetector 102 and illuminators 105-110 to controller 197. In other examples (not shown), controller may be separate from medical device 100.

Figure 2:
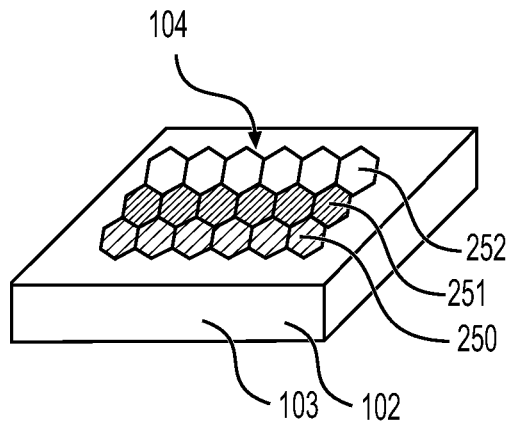
FIG. 2 is a photodetector assembly of the medical device of FIG. 1, according to aspects of this disclosure.

FIG. 2 shows a perspective view of photodetector 102 including a quantum dot structure 104 and a base 103. Photodetector 102 may include graphene, a titanium dioxide nanotube array, and a quantum dot structure 104 of quantum dots 250. Quantum dot structure 104 may include three different sized quantum dots 250-252, and quantum dot structure 104 may include any type of quantum dot known in the art. Quantum dot structure 104 may include a plurality of quantum dots arranged in a honeycomb structure, and base 103 may include graphene and/or one or more titanium dioxide nanotube arrays. Base 103 may be coupled to substrate 101 of medical device 100. In some examples, base 103 and/or quantum dot structure 104 may include a cross-linked structure of quantum dots 250-252, which may include covalent or ionic bonds linking quantum dots 250-252 together. In some examples, each quantum dot 250-252 of quantum dot structure 104 may be the same size, and in other examples quantum dot structure 104 may include one or more quantum dots of different sizes. For example, quantum dot 250 is shown as a different size from quantum dots 251, 252; and quantum dot 251 is shown as a different size from quantum dots 250, 252.

As shown in FIG. 2, quantum dot structure 104 may include a plurality of first quantum dots 250 (shown with wide cross-hatching) that are a first size, a plurality of second quantum dots 251 (shown with a narrow cross-hatching) that are a second size larger than the first size, and a plurality of third quantum dots 252 (shown without cross-hatching) that are a third size larger than the second size. In some examples, each of first quantum dots 250 may have a diameter of approximately 5 nm, each of second quantum dots 251 may have a diameter of approximately 7 nm, and each of third quantum dots 252 may have a diameter of approximately 10 nm. Quantum dots 250-252 may be all made of the same material, or may be made of different materials.

Figure 3A:
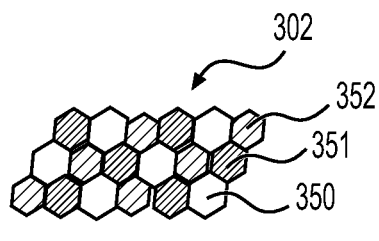
FIGS. 3A and 3B show different arrangements of cross-linked quantum dot arrays, according to aspects of this disclosure.
Figure 3B:
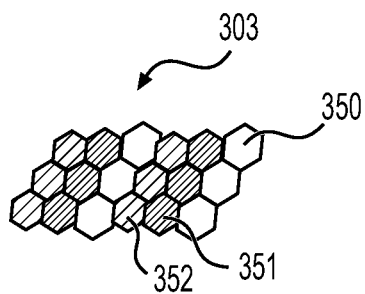

First quantum dots 250 may be CdSe quantum dots, second quantum dots 251 may be PbS quantum dots, and third quantum dots 252 may be ZnSe quantum dots. In other examples, first quantum dots 250 may be PbS quantum dots, and second and third quantum dots 251, 252 may be CdSe quantum dots. In further examples, each of first quantum dots 250, second quantum dots 251, and third quantum dots 252 may be different sizes of the same type of quantum dot, such as CdSe quantum dots. Quantum dots 250-252 may form an array. In some examples, quantum dot structure 104 may include over 1000 quantum dots. FIGS. 3A and 3B show alternative arrangements of quantum dot structures 302, 303 including first quantum dots 350, second quantum dots 351, and third quantum dots 352. First quantum dots, 350, second quantum dots 351, and third quantum dots 352 may be different sizes and/or different material, and/or may be the same size and/or material. Arrangements of quantum dots 350-351 shown in FIGS. 3A and 3B may be configured to evenly distribute the different sized quantum dots 350-352 across the surface area of the quantum dot structure 104. As shown in FIG. 3A, quantum dots 350 may be positioned abutting or adjacent to one or more of quantum dots 351, 352 and not other quantum dots 350, quantum dots 351 may be positioned abutting or adjacent to one or more of quantum dots 350, 352 and not other quantum dots 351; and quantum dots 352 may be positioned abutting or adjacent to one or more of quantum dots 350, 351 and not other quantum dots 350. As shown in FIG. 3B, quantum dots 352 may be arranged in a row and may be positioned between rows of quantum dots 351 and 350; quantum dots 351 may be arranged in a row and may be positioned between rows of quantum dots 350 and 352; and quantum dots 350 may be arranged in a row and may be positioned between rows of quantum dots 351 and 352. Any of the quantum dot structures 302, 303 of FIGS. 3A and 3B may be incorporated into photodetector 102.

Figure 4:
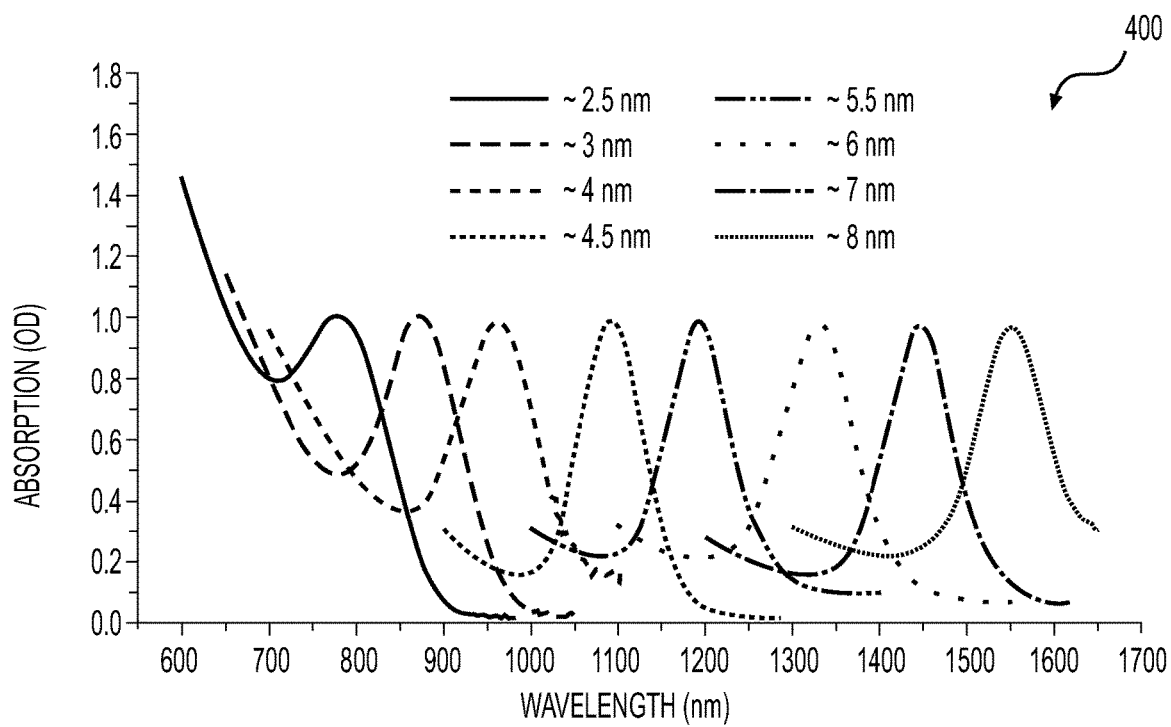
FIG. 4 shows a graph of the absorption of different wavelengths of light for eight different size quantum dots, according to aspects of the present disclosure.

FIG. 4 illustrates a graph 400 of the absorption profile for CdSe quantum dots of different sizes ranging from approximately 2.5 nm diameter to approximately 8 nm diameter. As shown in FIG. 4, the size of the quantum dot changes the sensitivity of the quantum dot to particular wavelengths of light, with higher absorption for specific ranges of light wavelength. For example, a CdSe quantum dot with a diameter of approximately 6 nm is sensitive to light with wavelengths between approximately 1300 nm and 1375 nm, while having much lower absorption of light with wavelengths of 1200 nm or less and wavelengths of 1400 nm or more.

By providing a photodetector 102 with different sized quantum dots 250-252, 350-352, medical device 100 may selectively activate particular sized quantum dots 250-252, 350-352 to adjust the sensitivity of photodetector 102 to particular wavelengths of light. In some examples, medical device 100 may selectively activate photodetector 102 via controller 197, and in other examples medical device 100 may selectively activate photodetector 102 via a controller wirelessly or otherwise electronically coupled to medical device 100 remote from medical device 100. In some examples, the photodetector 102 may activate and deactivate particular quantum dots 250-252, 350-352 to selectively adjust the sensitivity of photodetector 102 depending on which illuminator(s) 105-110 are activated at a particular time. For example, when one or more of illuminators 105-110 are activated to emit only infrared (IR) light, controller 197 may only activate quantum dots 350-352 that are sized such that the activated quantum dots 350-352 are sensitive to light with wavelengths between 780 nm and 1 mm (the infrared spectrum). By selectively activating quantum dots 350-352 with narrow frequency sensitivity, photodetector 102 may filter out unwanted noise without the use of a standard light filter.

Figure 5:
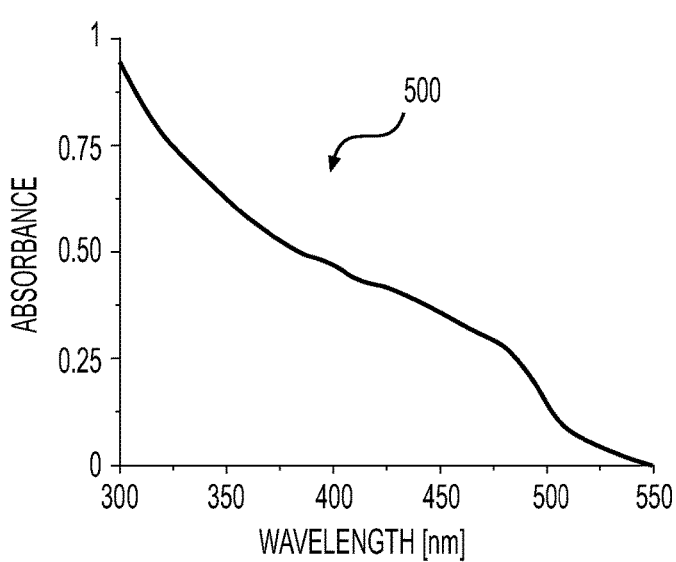
FIG. 5 shows the absorption of light at different wavelengths for a bulk size Cadmium Sulphide [CdS] photodetector, according to aspects of the present disclosure.
Figure 6:
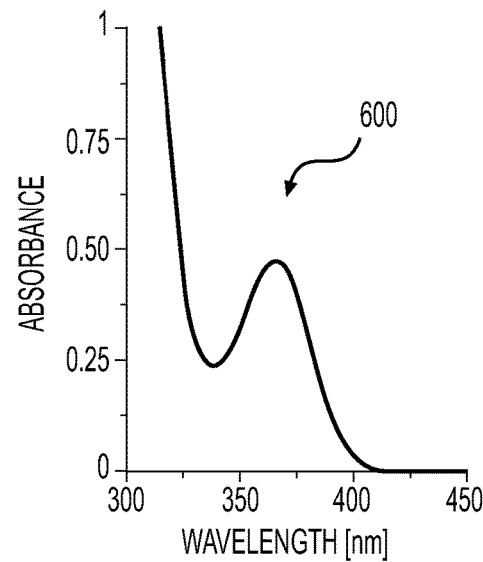
FIG. 6 shows the absorption of light at different wavelengths for a 4 nm CdS photodetector, according to aspects of the present disclosure.

FIG. 5 shows a graph of the absorption profile of a standard, bulk size CdS photodetector within the ultraviolet to visual spectra of light. As shown in FIG. 5, a bulk size CdS photodetector is sensitive to a broad range of wavelengths of light, and may be more susceptible to noise compared to a photodetector comprising an array of quantum dots. FIG. 6 shows the absorption profile, within the ultraviolet to visual spectra of light, of a photodetector comprising 4 nm size diameter CdS quantum dots. In view of the narrow peak between wavelengths 350 nm and 400 nm shown in FIG. 6, the photodetector comprising the 4 nm size diameter CdS quantum dots is more sensitive to a narrower range of wavelengths of light compared to the bulk size CdS photodetector.

Figure 7:
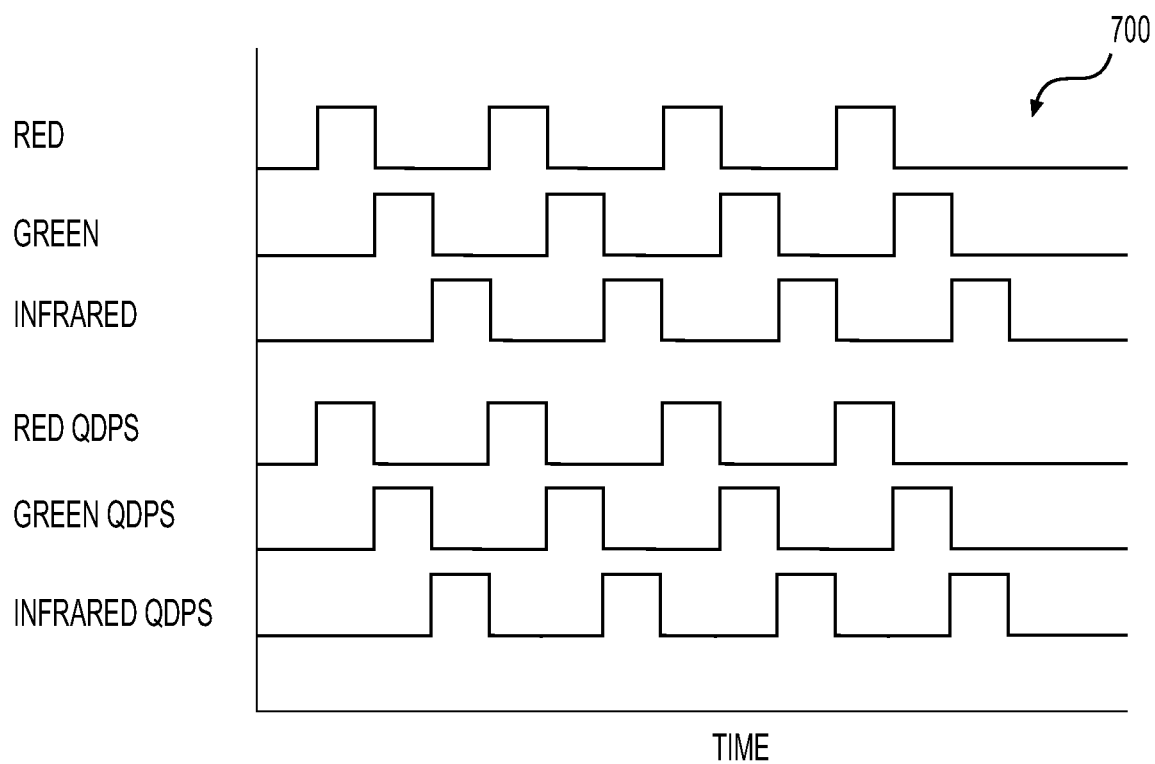
FIG. 7 shows a timing chart for selecting different color light emitting diodes and different quantum dot photodetectors, according to aspects of the present disclosure.

FIG. 7 illustrates a timing chart for selecting an illuminator 105-110 to activate and a particular size quantum dot 250-252 of photodetector 102 (quantum dot photodetectors, or "QDPS") to activate, in order to optimize the reflected light detected by photodetector 102 and limit the amount of noise detected by photodetector 102. In some examples, particular size quantum dots 250-252 may be activated for a faction of a second, and then a different set of particular size quantum dots 250-252 may be activated for a fraction of a second. In other examples, any other time interval may be used for activation of different sets of different size quantum dots 250-252. As shown in FIG. 7, the red illuminator(s) 105-110 may be activated when the red quantum dot photodetectors 250-252, 350-352 are activated on photodetector 102, the green illuminator(s) 105-110 may be activated when the green quantum dot photodetectors 250-252, 350-352 are activated on photodetector 102, and the infrared illuminator(s) 105-110 may be activated when the infrared quantum dot photodetectors 250, 350-352 are activated on photodetector 102. As discussed hereinabove, "red" quantum dot photodetectors 250-252, 350-352 may include quantum dots sized to be sensitive to light with wavelengths corresponding to red light, which in some examples may be light with wavelengths between 620 nm and 750 nm. Similarly, "green" quantum dot photodetectors 250-252, 350-352 may include quantum dots sized to be sensitive to light with wavelengths corresponding to green light, which in some examples may be light with wavelengths between 495 nm and 570 nm. "Infrared" quantum dot photodetectors 250-252, 350-352 may include quantum dots sized to be sensitive to light with wavelengths corresponding to infrared light, which in some examples may be light with wavelengths between 800 nm and 1 mm. By timing, or synchronizing, when quantum dots 250-252, 350-352 of a particular size are activated with the activation of a particular illuminator(s), medical device 100 may optimize the sensitivity of photodetector 102 for a particular wavelength of light being emitting by one or more illuminators 105-110. In some examples, a controller 197 of medical device 100 may be configured to activate and deactivate illuminators 105-110 and quantum dots 250-252, 350-352 in accordance with the timing chart of FIG. 7. For example, only quantum dots 250-252, 350-352 sized to be sensitive to infrared light may be activated when one or more infrared illuminators 105-110 is activated.

Figure 8:
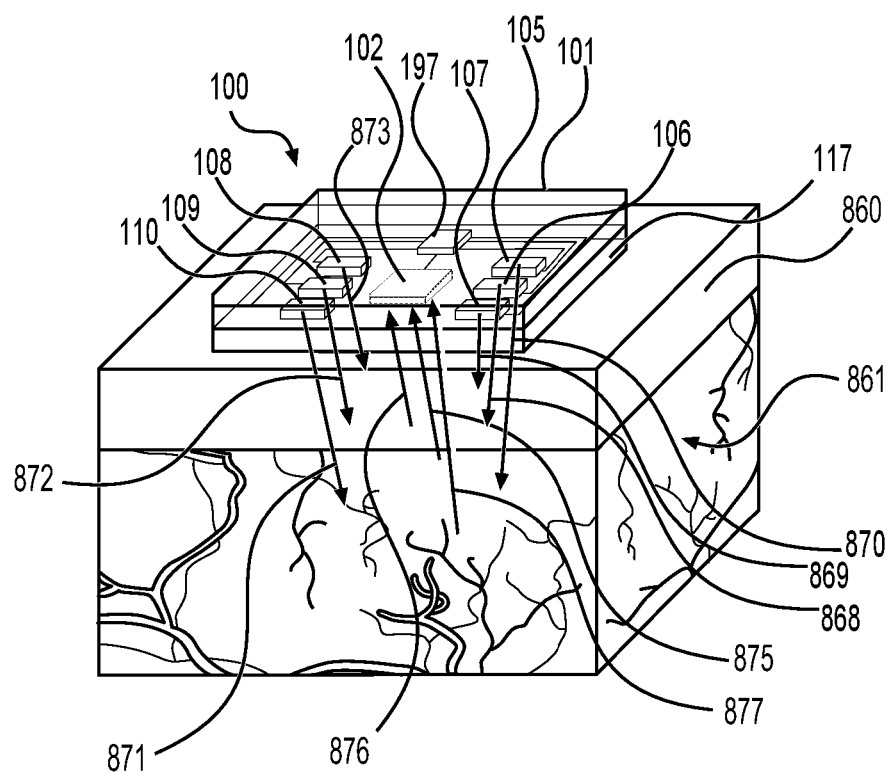
FIG. 8 shows the medical device of FIG. 1 coupled to a body, according to aspects of the present disclosure.

FIG. 8 shows medical device 100 coupled to a portion of skin 860 of a body of a user, with portions of the body of the user removed for clarity. Medical device 100 may be coupled to skin 860 via an adhesive, and controller 197 may control the emission of light from illuminators 105-110 into skin 860 and the interior portion 861 of the body. FIG. 8 illustrates representative arrows 868-873 showing light emitted from illuminators 105-110 into the interior portion 861 of the body of the user, and representative arrows 875-877 showing reflected light detected by photodetector 102. By fixing photodetector 102 of medical device 100 to the skin 860 of the user, movement of medical device 100 is limited relative to the body of the patient, which may facilitate optimizing signal sensitivity of photodetector 802. In some examples, medical device 100 may be configured to be an electrocardiogram (ECG or EKG) and measure electrical activity of a user's heartbeat. Medical device 100 may be configured to measure blood oxygen saturation, heart rate, respiration and cardiac output, blood pressure, volumetric variations of blood circulation, or any other physiological parameter measured via reflected (back-scattered) or transmitted light through tissue. In some examples, a first physiological parameter may be measured using a first one or more illuminators 105-110 emitting a first wavelength of light and detecting reflected light using one or more of a first size quantum dot 250-252, 350-352; and a second physiological parameter may be measured using a second one or more illuminators 105-110 emitting a second wavelength of light and detecting reflected light using one or more of a second size quantum dot 250-252, 350-352. In other examples, a first physiological parameter may be measured using a first one or more illuminators 105-110 emitting a first wavelength of light and detecting reflected light using one or more of a first size quantum dot 250-252, 350-352; and a second physiological parameter may be measured using the first one or more illuminators 105-110 emitting a second wavelength of light and detecting reflected light using one or more of a second size quantum dot 250-252, 350-352. Electrical signals from controller 197 may activate and/or deactivate different sized quantum dots 25-252, 350-353 and different illuminators 105-110. While medical device 100 is shown with a rectangular shape, medical device 100 may have any other suitable shape such as circular, oval, or ring-shaped. In some examples, medical device 100 may not include a hydrogel layer 117, and substrate 101 may be directly coupled to skin 860. In other examples, medical device 100 may only include a single illuminator 105-110.

Figure 9:
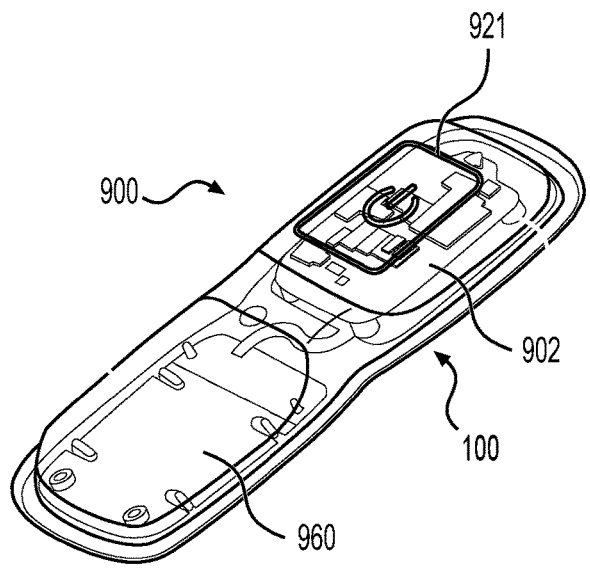
FIG. 9 shows a wearable medical device, according to aspects of the present disclosure.

FIG. 9 shows an alternative embodiment of a medical device 900 configured to couple to a user's body. Medical device 900 may have any of the features described herein in relation to medical device 100, and may include medical device 100 incorporated into the device (as shown). Medical device 900 may include a power source 960, and actuator 921 configured to turn on or off the device, a housing 902 configured to contain electronic components (such as electronic components of medical device 100) within a hermetically sealed cavity. Electronic components of medical device 100 may be positioned within body 902, and a substrate (such as substrate 101) may extend over body 902 and be configured to couple to a user's skin. In some examples, substrate 101 may be a medical adhesive tape and may extend over one or more openings in body 902. Body 902 may be flexible and the interior of body 902 may be sealed to prevent liquid penetration into the interior portion of body 902. Power source 960 may be a battery, such as a lithium ion battery or other battery known in the art. Controller 197 of medical device 100 (incorporated into medical device 900) may include one or more circuit boards, one or more processors, electronic storage, one or more antennas or wireless electronic communication devices, and/or non-transitory computer-readable medium.

Figure 10:
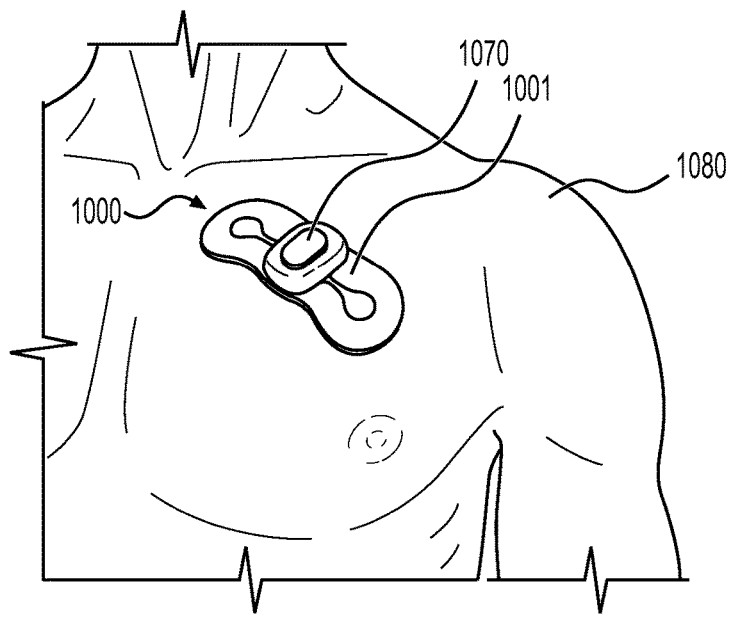
FIG. 10 shows a portion of a body with a medical device coupled to the body, according to aspects of the present disclosure.

FIG. 10 shows another embodiment of a medical device 1000 coupled to a body 1080 of a user. Medical device 1000 may have any of the features described herein in relation to medical devices 100, 900. Medical device 1000 may include a substrate 1001 configured to couple to a user's body 1080, and a body 1070 coupled to substrate 1001. Body 1070 may contain electronic components, such as one or more illuminators, photodetectors, controllers, power sources, antennas, etc. In some examples, one or more electronic components may be positioned within substrate 1001. Any of the components of medical device 100 may be positioned within housing 1070.

An exemplary method of operation is discussed herein below with relation to medical device 100, however any of the medical devices 100, 900, 1000 may be operated using the methods described herein. A user may first couple medical device 100 to the user's skin, for example via an adhesive on substrate 101. Medical device 100 may remain coupled to the user's body for a day, two days, three days, four days, five days, six days, a week, two weeks, a month, or any other suitable time period. One or more controllers 197 electronically connected to medical device 100 or included within medical device 100 may monitor one or more physiological parameters while medical device 100 is coupled to the user. Controller 197 may activate a first one or more quantum dots 250-252, 350-352 for a first time period and simultaneously activate a first one or more illuminators 105-110. The first quantum dots 250-252, 350-352 may each be of a first size, and the first one or more illuminators 105-110 may emit light within a first range of wavelengths towards the user's body. The one or more controllers 197 may then deactivate the first one or more quantum dots 250-252, 350-352 and the first one or more illuminators 105-110.

The one or more controllers 197 may then activate a second one or more quantum dots 250-252, 350-352 for a second time period and simultaneously activate a second one or more illuminators 105-110. The second one or more quantum dots 250-252, 350-352 and the second one or more illuminators 105-110 may be different from, partially different from, or the same as the first one or more quantum dots 250-252, 350-352 and the first one or more illuminators 105-110. In some examples, the second one or more quantum dots 250-252, 350-352 may include at least one quantum dot 250-252, 350-352 of a different size that the first one or more quantum dots 250-252, 350-352, and the second one or more illuminators 105-110 may emit light at a wavelength different from the light emitted from the first one or more illuminators 105-110. In some examples, the same illuminator 105-110 may be configured to emit different wavelengths of light depending on the instructions received from the one or more controllers 197. The one or more controllers 197 may also process one or more signals from photodetector 102 in order to measure one or more physiological parameters of the user.

It will be apparent to those skilled in the art that various modifications and variations may be made in the disclosed devices, systems, and methods without departing from the scope of the disclosure. It should be appreciated that the disclosed systems may include various suitable computer systems and/or computing units incorporating a plurality of hardware components, such as, for example, a processor and non-transitory computer-readable medium, that allow the systems to perform one or more operations during a method in accordance with those described herein. Other aspects of the disclosure will be apparent to those skilled in the art from consideration of the specification and practice of the features disclosed herein. It is intended that the specification and examples be considered as exemplary only.

It should be appreciated that the various systems may include any computing device. The computing device may include input and output ports to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

In one embodiment, any of the disclosed devices, systems, and/or methods may be executed by or implemented by a computing system consistent with or similar to the descriptions herein. Although not required, aspects of this disclosure are described in the context of computer-executable instructions, such as routines executed by a data processing device, e.g., a server computer, wireless device, and/or personal computer. Those skilled in the relevant art will appreciate that aspects of this disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "computing device," and the like, are generally used interchangeably herein, and refer to any of the above devices and systems, as well as any data processor.

Aspects of this disclosure may be embodied in a special purpose computer and/or data processor that is specifically programmed, configured, and/or constructed to perform one or more of the computer-executable instructions explained in detail herein. While aspects of this disclosure, such as certain functions, are described as being performed exclusively on a single device, this disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

It will be apparent to those skilled in the art that various modifications and variations can be made to the disclosed system, methods, and devices without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

I claim:

1. A medical device configured to couple to a body, the medical device comprising:
   a substrate configured to couple to a user's skin;
   a first illuminator configured to emit light at a first range of wavelengths;
   a second illuminator configured to emit light at a second range of wavelengths, wherein the second range of wavelengths is different from the first range of wavelengths
   a photodetector assembly comprising an array of quantum dot photodetectors, wherein the array of quantum dot photodetectors includes (i) a first quantum dot photodetector of a first size and configured to absorb light in the first range of wavelengths and (ii) a second quantum dot photodetector of a second size and configured to absorb light in the second range of wavelengths, wherein the first size is different from the second size; and
   a controller electronically coupled to the photodetector assembly, the first illuminator, and the second illuminator and configured to:
      deactivate the first quantum dot photodetector and the first illuminator when the second quantum dot photodetector and the second illuminator are activated; and
      deactivate the second quantum dot photodetector and the second illuminator when the first quantum dot photodetector and the first illuminator are activated.

2. The device of claim 1, further comprising at least one wire element positioned within the substrate, wherein the wire element is electrically coupled to the photodetector assembly, the first illuminator, and/or the second illuminator.

3. The device of claim 1, further comprising a hydrogel layer extending across the substrate, wherein the photodetector assembly, the first illuminator, and the second illuminator are positioned within the hydrogel layer.

4. The device of claim 1, wherein the controller is electronically coupled to the photodetector assembly, the first illuminator, and the second illuminator by one or more wire elements positioned within the substrate.

5. The device of claim 1, wherein:
   the first illuminator is configured to emit green light;
   the second illuminator is configured to emit red light;
   the first quantum dot photodetector is configured to absorb only green light; and
   the second quantum dot photodetector is configured to absorb only red light.

6. The device of claim 5, further comprising:
   a third illuminator configured to emit infrared light; and
   a third quantum dot photodetector configured to absorb only infrared light.

7. The device of claim 1, wherein:
   the first quantum dot photodetector includes a 5 nm diameter CdSe quantum dot;
   the second quantum dot photodetector includes a 7 nm diameter CdSe quantum dot; and
   the third quantum dot photodetector includes a 10 nm diameter PbS quantum dot.

8. The device of claim 1, wherein the array of quantum dot photodetectors is arranged in a single layer honeycomb structure in which each quantum dot photodetector of the array of quantum dot photodetectors only boarders other quantum dot photodetectors of a different size.

9. The device of claim 1, wherein:
   the controller is configured to measure a first physiological parameter when the first illuminator is activated and the second illuminator is deactivated, wherein the controller is configured to use data from the photodetector assembly to calculate the first physiological parameter, and
   the controller is configured to measure a second physiological parameter when the second illuminator is activated and the first illuminator is deactivated, wherein the controller is configured to use data from the photodetector assembly to calculate the second physiological parameter.

10. The device of claim 1, wherein the photodetector assembly includes graphene and/or one or more titanium dioxide nanotube arrays.

11. The device of claim 1, further comprising a body coupled to the substrate, wherein the photodetector assembly, the first illuminator, and the second illuminator are positioned within the body.

12. The device of claim 1, wherein the substrate is a medical tape configured to couple to skin of a user.

13. The device of claim 1, wherein the photodetector assembly is positioned between the first illuminator and the second illuminator.

14. The device of claim 1, wherein the array of quantum dot photodetectors includes at least 1000 quantum dots.

15. The device of claim 1, wherein the first quantum dot photodetector comprises a plurality of first quantum dots arranged in a row, and wherein the second quantum dot photodetector comprises a plurality of second quantum dots arranged in a row adjacent to the row of first quantum dots.

16. A medical device configured to couple to a body, the medical device comprising:
- a flexible substrate configured to couple to a user's skin;
- a photodetector assembly comprising an array of quantum dot photodetectors and one or more titanium dioxide nanotube arrays, wherein the array of quantum dot photodetectors includes a first quantum dot photodetector of a first size and a second quantum dot photodetector of a second size, wherein the first size is different from the second size;
- a first illuminator configured to emit light at a first range of wavelengths;
- a second illuminator configured to emit light at a second range of wavelengths, wherein the second range of wavelengths is different from the first range of wavelengths;
- a controller; and
- a wire element positioned on the flexible substrate and configured to electrically couple the first illuminator to the controller,
- wherein the controller is configured to alternatingly activate and deactivate the first quantum dot photodetector, the second quantum dot photodetector, the first illuminator, and the second illuminator according to predetermined time intervals.

17. The device of claim 16, wherein the array of quantum dot photodetectors includes a third quantum dot photodetector of a third size; and
wherein the first size is larger than the second size and the second size is larger than the third size.

18. The device of claim 17, wherein the first quantum dot photodetector includes a 5 nm diameter CdSe quantum dot, the second quantum dot photodetector includes a 7 nm diameter CdSe quantum dot, and the third quantum dot photodetector includes a 10 nm PbS quantum dot.

19. The device of claim 17, wherein the medical device is configured to measure at least one of: electrical activity of a user's heart, blood oxygen saturation, heart rate, respiration and/or cardiac output, blood pressure, and volumetric variations of blood circulation.

20. A method of measuring a physiological parameter using a medical device, the medical device comprising:
- a flexible substrate configured to couple to a user's skin;
- a photodetector assembly comprising an array of quantum dot photodetectors;
- a first illuminator configured to emit light at a first range of wavelengths; and
- a second illuminator configured to emit light at a second range of wavelengths, wherein the second range of wavelengths is different from the first range of wavelengths;

the method comprising:
- coupling the medical device to a body;
- activating a first quantum dot photodetector of the array of quantum dot photodetectors;
- emitting light from the first illuminator towards the body;
- receiving reflected light at the first quantum dot photodetector;
- deactivating the first quantum dot photodetector;
- activating a second quantum dot photodetector of the array of quantum dot photodetectors, wherein the second quantum dot photodetector is different from the first quantum dot photodetector and has a different size from the first quantum dot photodetector;
- emitting light from the second illuminator towards the body; and
- receiving reflected light at the second quantum dot photodetector.

* * * * *